United States Patent [19]

Portney et al.

[11] Patent Number: 5,053,171
[45] Date of Patent: Oct. 1, 1991

[54] MANUFACTURE OF OPHTHALMIC LENSES BY EXCIMER LASER

[75] Inventors: Valdemar Portney, Irvine; Albert C. Ting, Laguna Niguel; Timothy R. Willis, Lake Forest, all of Calif.

[73] Assignee: Allergan, Inc., Irvine, Calif.

[21] Appl. No.: 323,493

[22] Filed: Mar. 14, 1989

Related U.S. Application Data

[63] Continuation-in-part of Ser. No. 919,206, Oct. 14, 1986, Pat. No. 4,842,782.

[51] Int. Cl.$^5$ .................. B29D 11/00; B23K 26/06; C03B 23/00
[52] U.S. Cl. .................. 264/1.4; 65/102; 65/105; 65/112; 65/120; 219/121.61; 219/121.66; 219/121.67; 219/121.69; 219/121.73; 219/121.85; 264/25
[58] Field of Search .............. 264/1.4, 25; 65/102, 65/105, 112, 120; 219/121.61, 121.66, 121.67, 121.69, 121.73, 121.85

[56] References Cited

U.S. PATENT DOCUMENTS

| | | | |
|---|---|---|---|
| 3,410,203 | 11/1968 | Fischbeck | 101/1 |
| 3,440,388 | 4/1969 | Otstot et al. | 219/69 |
| 3,549,733 | 12/1970 | Caddell | 264/25 |
| 3,657,085 | 4/1972 | Hoffmeister et al. | 219/121 |
| 3,742,182 | 6/1973 | Saunders | 219/127 |
| 3,972,599 | 8/1976 | Engel et al. | 331/94.5 |
| 4,032,861 | 6/1977 | Rothrock | 331/945 |
| 4,081,655 | 3/1978 | Gale | 219/121 LJ |
| 4,108,659 | 8/1978 | Dini | 156/634 |
| 4,128,752 | 12/1978 | Gravel | 219/121 L |
| 4,147,402 | 4/1979 | Chown | 264/1.4 |
| 4,156,124 | 5/1979 | Macken et al. | 219/121 |
| 4,194,814 | 3/1980 | Fischer et al. | 351/160 R |
| 4,219,721 | 8/1980 | Kamen et al. | 264/1.4 |
| 4,275,288 | 6/1981 | Makosch et al. | 219/121 LR |
| 4,307,046 | 12/1981 | Neefe | 264/1.4 |
| 4,323,317 | 4/1982 | Hasegawa | 400/118 |
| 4,370,175 | 1/1983 | Levatter | 148/1.5 |
| 4,402,579 | 9/1983 | Poler | 351/160 R |
| 4,414,059 | 11/1983 | Blum et al. | 156/659 |
| 4,430,548 | 2/1984 | Macken | 219/121 LG |
| 4,450,593 | 5/1984 | Poler | 3/13 |
| 4,455,893 | 6/1984 | Astero | 76/107 |
| 4,473,735 | 9/1984 | Steffen | 51/285 |
| 4,510,005 | 4/1985 | Nijman | 264/1.4 |
| 4,556,524 | 12/1985 | Cullis et al. | 264/1.4 |
| 4,563,565 | 1/1986 | Kampfer et al. | 219/121 |
| 4,642,439 | 2/1987 | Miller et al. | 264/1.4 |
| 4,644,130 | 2/1987 | Bachmann | 219/121 LJ |
| 4,652,721 | 3/1987 | Miller et al. | 264/1.4 |
| 4,665,913 | 5/1987 | L'Esperance, Jr. | 128/303.1 |
| 4,669,466 | 6/1987 | L'Esperance | 128/303.1 |
| 4,718,418 | 1/1988 | L'Esperance, Jr. | 128/303.1 |
| 4,721,379 | 1/1988 | L'Esperance, Jr. | 128/303.1 |
| 4,729,372 | 3/1988 | L'Esperance, Jr. | 128/303.1 |
| 4,732,148 | 3/1988 | L'Esperance, Jr. | 128/303.1 |
| 4,770,172 | 9/1988 | L'Esperance, Jr. | 128/303.1 |
| 4,773,414 | 9/1988 | L'Esperance, Jr. | 128/303.1 |
| 4,798,204 | 1/1989 | L'Esperance, Jr. | 128/303.1 |
| 4,842,782 | 6/1989 | Portney et al. | 264/1.4 |
| 4,856,513 | 8/1989 | Muller | 350/363 |

FOREIGN PATENT DOCUMENTS

| | | |
|---|---|---|
| 1038935 | 9/1978 | Canada. |
| 2546692 | 4/1977 | Fed. Rep. of Germany. |
| 2510768 | 7/1982 | France. |
| 29627 | 2/1983 | Japan. |
| 97787 | 6/1984 | Japan. |
| WO87/05496 | 9/1987 | World Int. Prop. O. |

OTHER PUBLICATIONS

"Laser Applications in Semiconductor Microlithography"; Kanti Jain; Lasers & Applications; Sept. 1983, pp. 49–56.

(List continued on next page.)

Primary Examiner—James Lowe
Attorney, Agent, or Firm—Gordon L. Peterson; Loyal M. Hanson

[57] ABSTRACT

Complex small objects such as ophthalmic lenses are quickly and accurately fabricated from plastic or glass blanks of ablatable material such as plastic or glass by cutting, shaping, and radiusing the blank entirely by laser light, using appropriate masks with focusing and imaging optics.

40 Claims, 2 Drawing Sheets

OTHER PUBLICATIONS

"Effective Deep Ultraviolet Photoetching of Polymethyl Methacrylate by an Excimer Laser"; Y. Kawamura, K. Toyoda and S. Namba; Appl. Phys. Lett. 40(5), 1 Mar. 1982; pp. 374–375.

"Deep-Ultraviolet Spatial-Period Division Using an Excimer Laser", A. M. Hawryluk and Henry I. Smith; Optic Letters; vol. 7, No. 9, Sept. 1983; pp. 402–404.

"Laser Ablation of Organic Polymers: Microscopic Models for Photochemical and Thermal Processes"; B. Garrison et al., Journal of Applied Physics, 57(8); Apr. 15, 1985; pp. 2909–2914.

"Kinetics of the Ablative Photodecomposition of Organic Polymers in the Far-Ultraviolet (193 nm)"; IBM Thomas J. Watson Research Center; pp. 1–11.

"Action of Far-Ultraviolet Light on Organic Polymer Films: Applications to Semiconductor Technology", IBM Thomas J. Watson Research Center; pp. 1–9.

MANUFACTURE OF OPHTHALMIC LENSES BY EXCIMER LASER

CROSS REFERENCE TO RELATED APPLICATION

This application is a continuation in part of copending U.S. Patent Application Serial No. 919,206 filed Oct. 14, 1986, from which issued U.S. Pat. No. 4,842,782.

BACKGROUND OF THE INVENTION

1. Technical Field

The invention relates generally to the manufacture of ophthalmic lenses such as contact, corneal implant, and intraocular lenses, and other small plastic or glass objects of similar shape, and more particularly to a method of making such lenses or objects with a high degree of precision at low cost by using an excimer laser.

2. Background Information

Ophthalmic lenses are normally manufactured by a mechanical process in which a block of polymehthylmethacrylate (PMMA) is machined while being adhesively held on a support. The machining is quite difficult because of the small size of the lens and the intricacy of the shape into which the lens must be machined.

Typically, three operations must be performed to shape a lens. For one, the workpiece must be cut out from a blank to form, for example, an integral optic and haptic. In addition, the surface of the workpiece must be machined to the desired optical specifications, which may include convexities or concavities of varying radii at different points on the surface of the lens, and the edges of the workpiece must be radiused or rounded.

In the prior art, the edge rounding step alone typically required 7-14 days of gemstone tumbling, and precision was hard to accomplish in all of the steps.

SUMMARY OF THE INVENTION

The present invention provides a method of fabricating ophthalmic lenses or similar small objects quickly and accurately by using a laser, and particularly an excimer laser, to cut, surface-model, and bevel a workpiece which is preferably made of PMMA but may, for appropriate purposes, be made of other plastics or of glass. The type and tuning of the laser is dependent upon the material of the blank.

In accordance with the invention, the workpiece is first cut to shape by shining a laser beam through a mask outlining the form of the cut required to shape (in the case of an ophthalmic lens) the optic and haptic. Considerable precision can be obtained in this step by expanding the laser beam in front of the mask and then reducing it beyond the mask to provide fine detail from a relatively large mask. The depth of the cut can be controlled by the number and energy of the pulses.

The surface modeling of the lens is next achieved by masking a laser beam in such a way that its energy distribution varies across the surface of the workpiece so as to ablate it to differing degrees at different points of the surface. This can be achieved by using a mask of varying opacity or a semi-transparent mirror with a coating of varying thickness at different points on the surface. This step, if desired, may be performed before the cutting step.

Finally, a laser beam is masked and focused generally into the form of a hollow cone whose tip is the focal point of the beam. By exposing the workpiece to the beam on one side of the focal point and then on the other, two bevel cuts are made along the perimeter of the upper and lower surfaces, respectively, of the workpiece. When combined with a vertical section of the side of the workpiece, these bevel cuts form an approximation of a rounded edge which is further softened by the slight melting of the workpiece material produced by the heat generated by the laser during cutting.

It is therefore the object of the invention to quickly and accurately produce a complex small object such as an ophthalmic lens from a blank entirely by the use of a laser.

According to another aspect of the invention, the method is modified in order to alleviate two concerns. One concern is that shining or projecting the laser beam toward the workpiece can be accompanied by some diffraction that may result in some distortion at the workpiece that can degrade resolution. Another concern is that mask size may have to approximate workpiece size and the laser beam may have to be expanded to cover the entire mask and the workpiece surface.

These problems are solved by adding the step of imaging to the step of laser beam projection previously described. In other words, a lens of one or more optical elements disposed intermediate the mask and the workpiece images the mask (i.e., the pattern on the mask) onto the workpiece. Better resolution can be had, mask size can be reduced, and beam expansion can be eliminated.

Generally, a method of making small objects from a blank of ablatable material according to this aspect of the invention includes at least one of the steps of (1) cutting a workpiece from the blank by exposing the blank to laser light in the outline of said workpiece without focusing the laser light at the workpiece, (2) exposing the surface of said workpiece to laser light through a mask having areas transmitting said light in varying degrees, and (3) shaping the edges of said workpiece by exposing them to an inclined beam of laser light, that step being performed so that it includes imaging the outline or pattern on the blank to achieve the advantages described above.

The above mentioned and other objects and features of this invention and the manner of attaining them will become apparent, and the invention itself will be best understood, by reference to the following description taken in conjunction with the accompanying illustrative drawings.

DESCRIPTION OF THE PREFERRED EMBODIMENTS

In the preferred embodiment of the invention, which is the manufacture of ophthalmic lenses from a PMMA blank, the method of this invention is carried out with an excimer laser, that is a laser operating in the high ultraviolet wavelengths. An argon-fluoride laser operating at a wavelength of 193 nm in 250 millijoule pulses is preferred, but broadly any ultraviolet wavelength substantially absorbed by the material of the workpiece may be used. The choice of the laser is dictated by its ability to break up the large molecules of the workpiece material (as in the case of plastic) or to melt the material (as in the case of glass) so that the material will ablate.

Figure 1:
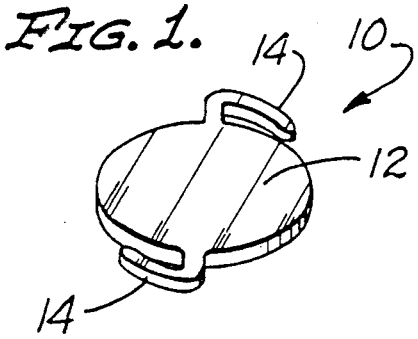
FIG. 1 is a perspective view of an intraocular lens to be manufactured by the method of this invention.

FIG. 1 shows a typical intraocular lens which may be produced by the method of this invention. The workpiece 10 has an optic 12 which forms the actual lens, and a haptic 14 by which the lens is anchored in the patient's eye. In the prior art, polypropylene is usually used for the haptic 14, and PMMA is used for the optic 12. However, both the optic 12 and the haptic 14 may be formed of PMMA, and in the process of this invention this is preferable because the entire workpiece can be cut as a single piece. Of course, other ultraviolet-absorbing materials than PMMA (e.g. silicone) may be used for the workpiece if they are medically acceptable and properly ablatable.

Figure 3:
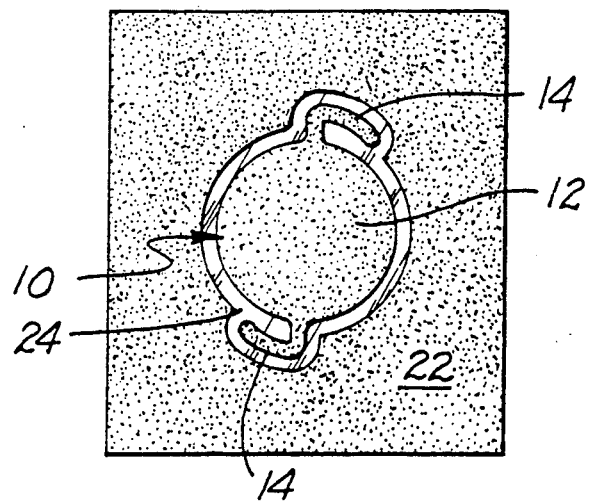
FIG. 3 is a plan view of the mask used in the cutting step.
Figure 2:
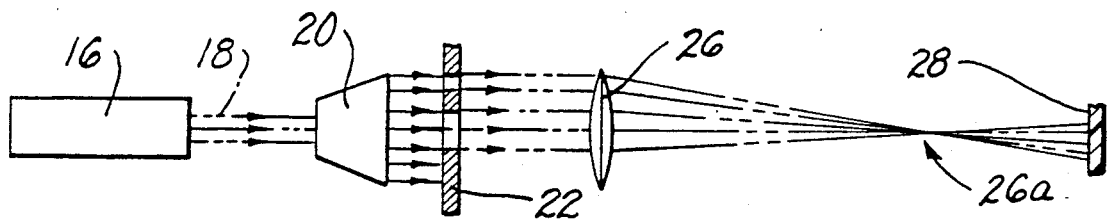
FIG. 2 is a schematic diagram of a laser optic used in the cutting step of the invention.

FIG. 2 shows an arrangement useful in cutting the workpiece 10 from a block of PMMA. An excimer laser 16 emits a beam 18 of coherent ultraviolet light. Because the diameter of beam 18 is fairly small, a conventional laser beam expander 20 is used to expand the beam 18 to a diameter of several centimeters. A mask 22 best shown in FIG. 3 is formed integrally with the beam expander 20 or placed into the path of the expanded beam 18 to allow only a narrow strip of light in the shape of the outline 24 of the workpiece 10 to pass through the mask 22. As shown in FIG. 2, the laser energy entering the mask 22 is collimated.

A beam converger or focusing optic 26 is used to project a reduced image of the outline 24 onto the PMMA block 28. Repeated pulses of the laser 16 will ablate the material of the block 28 until the profiled lens or workpiece 10 is very precisely cut out of the block 28. The precision of the cut is enhanced (and the power density of the beam increased) by the use of a relatively large mask 22 and a substantial reduction of the mask image on the block 28.

Alternatively, the focusing optic 26 (which in this embodiment is a biconvex optical element) can include a lens of one or more elements configured according to known techniques to image the outline 24 on the block 28. In other words, the step of cutting a workpiece from said blank includes imaging the outline of said workpiece on said blank. This results in the beam having a focal point 26a intermediate the focusing optic 26 and the block 28 and, preferably, it is done so that the beam expander 20 is not needed and can be omitted.

After being cut out from the block 28, the workpiece 10 is placed into the path of an excimer laser beam 30 (FIG. 4) which has a uniform energy distribution across its area. A mask 32 is interposed between the workpiece 10 and the beam 32.

Figure 5:
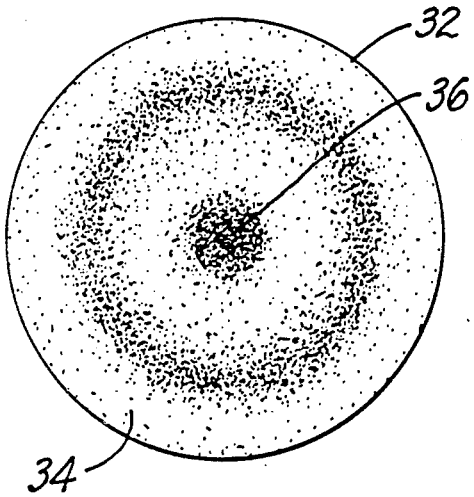
FIG. 5 is a plan view of the mask used in the surface modeling step.

As best shown in FIG. 5, the mask 32 has different degrees of transparency at different points on the mask 32. For example, the mask 32 may have a coating of variable or non-uniform transmission characteristics, or it may be a neutral density filter (such as a polarizing or haze filter) with non-uniform transmission characteristics. In any event, the mask 32 transmits a large amount of beam energy in the areas 34 corresponding to desired depressions in the workpiece 10, and a small amount in the areas 36 corresponding to desired protrusions in the workpiece 10.

By appropriately controlling the transmission characteristics of the mask 32, it is possible to model or shape the surface 38 of the workpiece 10 in any desired manner without complex machining, and to do so precisely in a small amount of time. An imaging optic arrangement 32a (FIG. 4) can be located intermediate the mask 32 and the workpiece 10 in order to image the mask 32 (i.e., the pattern on the mask) on the workpiece 10. In other words, the step of exposing the surface of said workpiece to laser light includes imaging the mask on said workpiece. Such an imaging optic arrangement 32a includes a lens of one or more elements configured according to known techniques to have a focal point 32b intermediate the imaging optic arrangement 32a and the workpiece 10 in order to image the mask 32 (i.e., the pattern on the mask 10) on the workpiece 10, and imaging in this way achieves the advantages previously mentioned. The mask 32 can be combined with the mask 22 to conduct shaping and cutting simultaneously.

In an alternative embodiment of the invention, the mask 32 may take the form of a semi-transparent mirror with a reflective coating whose thickness varies along its surface. In that embodiment, the laser energy not used for ablation is reflected away from the workpiece.

Figure 4:
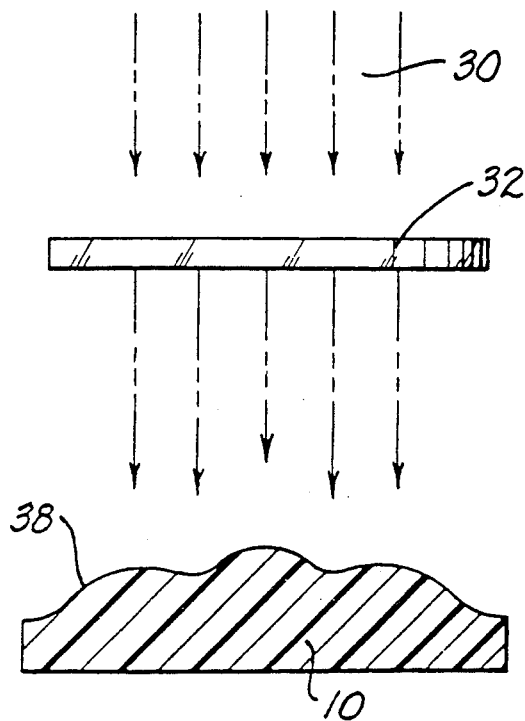
FIG. 4 is a schematic diagram illustrating the surface modeling step of this invention.

After the shaping or modeling step of FIGS. 4 and 5, the workpiece is fully formed but has sharp vertical edges which are not suitable for intraocular use. In the prior art, the edges of the workpiece were radiused or rounded by gemstone tumbling for 7-14 days, but besides being time-consuming, this prior art method often defeated the carefully achieved precision of the workpiece.

In accordance with the invention, an excimer laser beam 40 (FIG. 6) is expanded by a beam expander or (preferably) by a pair of curved mirrors 42 and 44. The use of reflective rather than refractive beam expanding optics is preferred because it permits higher power transfer with smaller optics while avoiding damage to the optics.

Figure 6:
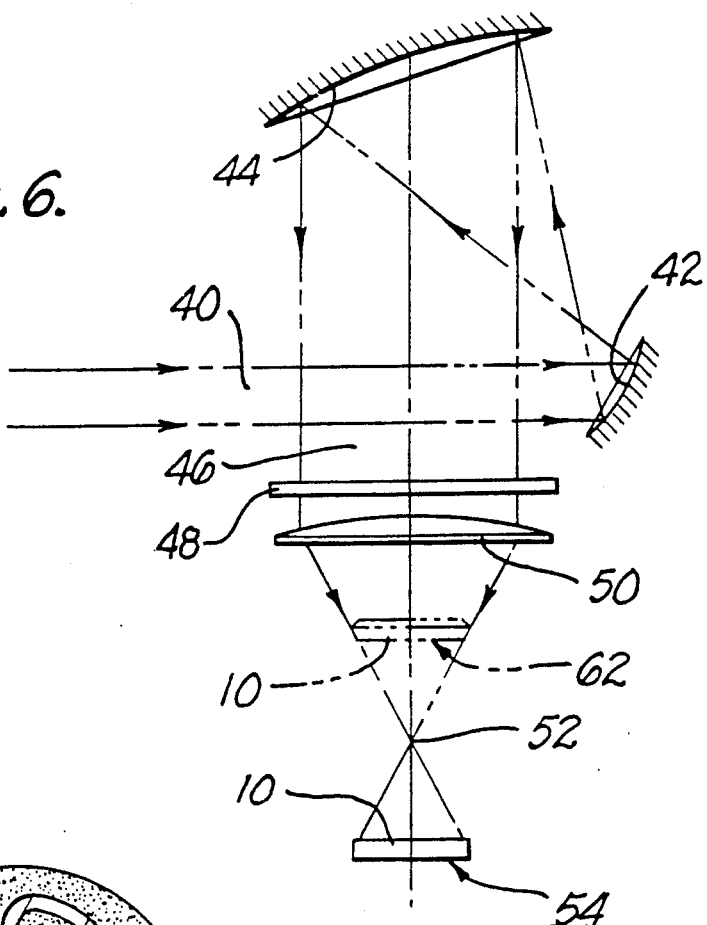
FIG. 6 is a schematic diagram illustrating the edge beveling step of this invention.
Figure 7:
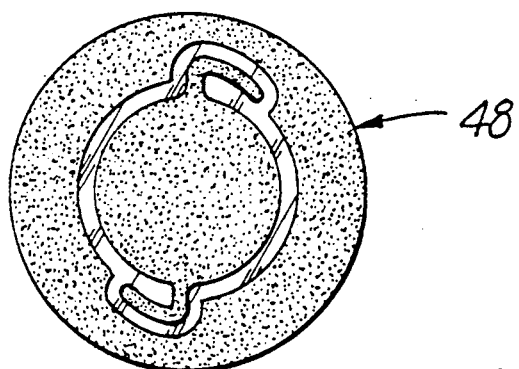
FIG. 7 is a plan view of the mask used in the beveling step.

The expanded beam 46 is conducted through a mask 48 best shown in FIG. 6 to a focusing lens 50. As a result, a beam generally in the form of a hollow cone is produced, with the tip of the cone being the focal point 52. The beveling of one side can be achieved during the cutting operation to expedited the overall process.

Figure 8:
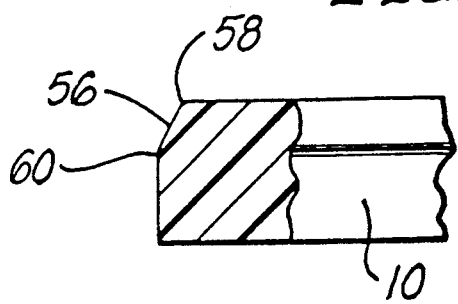
FIG. 8 is a fragmentary detail section of the workpiece after the first beveling step.

In order to round its edges, the workpiece 10 is first positioned below the focal point 52 at 54, and the laser is turned on. The conical shape of the beam will produce a bevel 56 (FIG. 8) on the edges of the workpiece 10, the focusing lens 50 being configured to image the mask 48 on the workpiece 10. The ends of the bevel 56 are slightly rounded at 58 and 60 by the small amount of heat which is produced during the ablation of workpiece material which forms the bevel 56.

Figure 9:
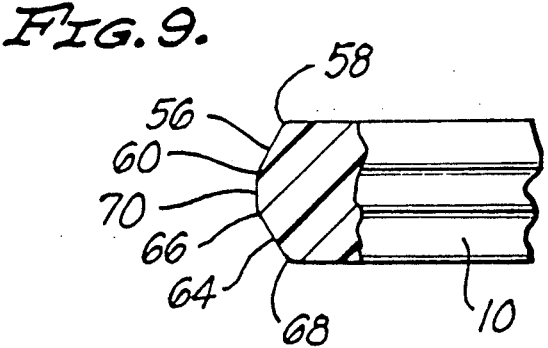
FIG. 9 is a fragmentary detail section of the workpiece after the second beveling step.

When the bevel 56 has been fully formed, the workpiece 10 is positioned above the focal point 52 at 62, and the beam is turned on again. This time, the conical shape of the beam results in cutting a bevel 64 (FIG. 9) whose edges are slightly rounded at 66 and 68 for the same reason as described above.

When combined with the vertical surface 70, the bevels 56 and 64 and their rounded extremities provide a sufficient approximation of a rounded edge for the workpiece 10 to make it suitable for implantation in a patient's eye without danger of irritation.

It will be seen that the above-described process provides a fast and accurate way of manufacturing intraocular lenses without the use of complex machining equipment. The invention can, of course, be carried out with variations. For example, a very narrow laser beam may be moved around the periphery of the workpiece in the cutting and beveling steps, rather than cutting or beveling the entire periphery at once, or a mask may be scanned rather than being exposed all at once.

Although an exemplary embodiment of the invention has been shown and described, many changes, modifications, and substitutions may be made by one having ordinary skill in the art without necessarily departing from the spirit and scope of the invention. For example, many of the steps in the following claims can be combined and such combinations are intended to fall within the scope of the claims.

What is claimed is:

1. A method of making small objects from a blank of ablatable material, comprising the steps of:
   cutting a workpiece from said blank by exposing said blank to laser light in the outline of said workpiece without focusing the laser light at the workpiece;
   exposing the surface of said workpiece to laser light through a mask having areas transmitting said light in varying degrees;
   beveling the edges of said workpiece by exposing them to an inclined beam of laser light; and
   wherein the step of cutting a workpiece from said blank includes focusing laser light in the outline of said workpiece at a location and placing the blank beyond the location so as to image the outline of the workpiece on said blank.

2. The method of claim 1, in which said laser light is in the ultraviolet range.

3. The method of claim 1, in which said material is a plastic material.

4. The method of claim 3, in which said material is polymethylmethacrylate.

5. The method of claim 1, in which said material is glass.

6. The method of claim 1, in which said workpiece is an opthalmic lens having an optic and a haptic formed as a single piece.

7. A method of making small objects from a blank of ablatable material, comprising the steps of:
   cutting a workpiece from said blank by exposing said blank to laser light in the outline of said workpiece without focusing the laser light at the workpiece;
   exposing the surface of said workpiece to laser light passing through a mask with the mask having areas transmitting said light in varying degrees;
   beveling the edges of said workpiece by exposing them to an inclined beam of laser light; and
   wherein the step of exposing the surface of said workpiece to laser light includes focusing the laser light which passes through the mask at a location and placing the surface beyond the location so as to image the mask on said workpiece.

8. The method of claim 7, in which said laser light is in the ultraviolet range.

9. The method of claim 7, in which said material is a plastic material.

10. The method of claim 9, in which said material is polymethylmethacrylate.

11. The method of claim 7, in which said material is glass.

12. The method of claim 7, in which said workpiece is an ophthalmic lens having an optic and a haptic formed as a single piece.

13. A method comprising:
    directing laser energy through a mask without focusing the laser energy at the mask and with the mask having variable transmissivity characteristics to the laser energy to provide a first laser beam of variable energy across its width;
    focusing the first laser beam of variable energy at a location and placing a surface beyond the location so as to image the mask on the surface; and
    allowing the first laser beam of variable energy to impinge on the surface for a sufficient time to remove material from multiple locations on the surface in accordance with said characteristics with more of the material being removed at one of the locations than is removed at another of the locations.

14. A method as defined in claim 13 wherein the surface generally faces in the direction from which the laser energy is directed.

15. A method as defined in claim 13 wherein said surface is on a workpiece and the characteristics of the mask are such that the first laser beam shapes the surface of the workpiece into an ophthalmic lens.

16. A method as defined in claim 13 wherein the laser energy is excimer laser energy.

17. A method as defined in claim 13 including cutting a workpiece from a blank by exposing the blank to laser energy in the outline of said workpiece and said surface is on the workpiece.

18. A method as defined in claim 17 including beveling an edge of the workpiece by exposing it to laser energy.

19. A method as defined in claim 13 including directing a second laser beam toward a blank in a pattern without focusing the second laser beam at the blank for a sufficient length of time to cut a workpiece from the blank and said surface is on the workpiece.

20. A method as defined in claim 19 wherein the step of directing the second laser beam toward the blank includes directing the second laser beam through a mask with the second laser beam passing through the mask being in said pattern.

21. A method as defined in claim 19 wherein the laser energy is directed toward the blank to cut the workpiece from the blank without relatively moving the workpiece and the pattern.

22. A method as defined in claim 19 including directing laser energy through a mask to the workpiece without focusing the laser energy at the workpiece to bevel an edge of the workpiece.

23. A method as defined in claim 13 including beveling an edge of a workpiece by exposing it to laser energy and said surface is on the workpiece.

24. A method as defined in claim 13 including directing laser energy through a mask to a workpiece without focusing the laser energy at the workpiece to bevel an edge of the workpiece and said surface is on the workpiece.

25. A method comprising:

directing the laser energy through a mask without focusing the laser energy at the mask and with the mask having variable reflectivity or variable transmissivity characteristics to the laser energy to provide a first laser beam of variable energy across its cross section;

focusing the first laser beam of variable energy at a location and placing a surface beyond the location so as to image the mask on the surface; and allowing the first laser beam of variable energy to impinge on the surface for a sufficient time to remove material from multiple locations on the surface in accordance with said characteristics with more of the material being removed at one of the locations on the surface than is removed at another of the locations on the surface.

26. A method as defined in claim 25 wherein said step of allowing is carried out without relatively moving the laser beam and the surface.

27. A method as defined in claim 26 wherein said characteristics are such that the first laser beam shapes the surface into an ophthalmic lens.

28. A method as defined in claim 26 wherein said characteristics are such that the first laser beam shapes the surface into a curve.

29. A method as defined in claim 25 including cutting a workpiece from a blank by exposing the blank to laser energy in the outline of said workpiece and said surface is on the workpiece.

30. A method as defined in claim 25 including beveling an edge of a workpiece by exposing it to laser energy and said surface is on the workpiece.

31. A method as defined in claim 25 wherein said characteristics of the mask provide the first laser beam with continuously variable energy across a portion of its cross section and said step of allowing removes material from said multiple locations on the surface to curve the surface.

32. A method as defined in claim 25 wherein said multiple locations on the surface are contiguous.

33. A method as defined in claim 25 wherein the step of directing of the laser energy through a mask is accompanied by some diffraction that would result in some distortion at the surface that degrades resolution and the imaging of the mask on the surface improves said resolution.

34. A method as defined in claim 33 wherein said step of allowing is carried out without relatively moving the laser beam and the surface and said characteristics are such that the first laser beam shapes the surface into a curve.

35. A method for cutting a workpiece from an object comprising:

directing laser energy through a mask toward an object without focusing the laser energy on the mask or the object and with the laser energy passing through the mask being in a pattern in the outline of the workpiece, focusing the laser energy passing through the mask at a location, placing the object beyond the location so as to image the outline of the workpiece on the object, and exposing the object to the laser energy for a sufficient length of time to allow the laser energy to cut the workpiece having the shape of said pattern from the object.

36. A method as defined in claim 35 wherein the laser energy is directed toward the object to cut the workpiece from the object without relatively moving the object and the pattern.

37. A method as defined in claim 35 including beveling an edge of the workpiece by exposing it to laser energy.

38. A method as defined in claim 35 including directing laser energy through a mask to the workpiece without focusing the laser energy at the workpiece to bevel an edge of the workpiece.

39. A method as defined in claim 35 wherein said pattern is generally in the shape of an intraocular lens.

40. A method as defined in claim 35 including collimating the laser energy entering the mask.

* * * * *